US010463593B2

(12) United States Patent
Baudouin et al.

(10) Patent No.: US 10,463,593 B2
(45) Date of Patent: Nov. 5, 2019

(54) LUPIN PEPTIDE EXTRACTS AND SKIN FIRMNESS

(71) Applicant: LABORATOIRES EXPANSCIENCE, Courbevoie (FR)

(72) Inventors: Caroline Baudouin, Rambouillet (FR); Sophie Leclere-Bienfait, Dreux (FR); Philippe Msika, Versailles (FR); Stéphanie Bredif, Croisilles (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 63 days.

(21) Appl. No.: 15/323,347

(22) PCT Filed: Jul. 3, 2015

(86) PCT No.: PCT/EP2015/065254
§ 371 (c)(1),
(2) Date: Dec. 30, 2016

(87) PCT Pub. No.: WO2016/001430
PCT Pub. Date: Jan. 7, 2016

(65) Prior Publication Data
US 2017/0157019 A1 Jun. 8, 2017

(30) Foreign Application Priority Data

Jul. 3, 2014 (FR) .................................. 14 56385

(51) Int. Cl.
*A61K 8/64* (2006.01)
*A61Q 19/06* (2006.01)
(Continued)

(52) U.S. Cl.
CPC ............... *A61K 8/645* (2013.01); *A61K 8/97* (2013.01); *A61Q 19/06* (2013.01); *A61Q 19/08* (2013.01); *A61K 2800/74* (2013.01)

(58) Field of Classification Search
None
See application file for complete search history.

(56) References Cited

U.S. PATENT DOCUMENTS 7,638,149 B2 * 12/2009 Msika .................... A61K 8/645
424/725
2005/0148498 A1 7/2005 Msika et al.
(Continued)

FOREIGN PATENT DOCUMENTS

| FR | 2 792 202 A1 | 10/2000 |
| FR | 2 893 252 A1 | 5/2007 |
| WO | WO 02/15869 A1 | 2/2002 |

OTHER PUBLICATIONS

Database GNPD [Online] Mintel, "Lotion," Narüko, Database Accession No. 2337946, Apr. 2014, pp. 1-7. (Year: 2014).*
(Continued)

*Primary Examiner* — Carlos A Azpuru
*Assistant Examiner* — Casey S Hagopian
(74) *Attorney, Agent, or Firm* — Birch Stewart Kolasch & Birch, LLP

(57) ABSTRACT

The present invention relates to the use of a lupin peptide extract to prevent loss of skin firmness or to increase the firmness of skin. Advantageously, the lupin peptide extract can prevent the appearance of cellulite and/or reduce skin cellulite.

21 Claims, 4 Drawing Sheets

(51) Int. Cl.
*A61Q 19/08* (2006.01)
*A61K 8/97* (2017.01)

(56) References Cited

U.S. PATENT DOCUMENTS

| | | |
|---|---|---|
| 2007/0184012 A1 | 8/2007 | Perrier et al. |
| 2008/0153757 A1 | 6/2008 | Beeson et al. |
| 2011/0002969 A1* | 1/2011 | Serraima ............... A61K 8/64 424/401 |
| 2011/0034486 A1 | 2/2011 | Meyer et al. |

OTHER PUBLICATIONS

Database GNPD [Online] Mintel, "Lotion," Narüko, Database Accession No. 2337946, Apr. 2014, pp. 1-7.

Kligman et al., "Topical retinol improves cellulite," Journal of Dermatological Treatment, vol. 10, Issue 2, 1999 (published online Jul. 12, 2009), pp. 119-125 (8 pages).

Written Opinion of the International Searching Authority and International Search Report (Forms PCT/ISA/237 and PCT/ISA/210), dated Sep. 15, 2015, for International Application No. PCT/EP2015/065254.

\* cited by examiner

LUPIN PEPTIDE EXTRACTS AND SKIN FIRMNESS

FIELD OF THE INVENTION

The present invention relates to the use of a lupin peptide extract to prevent loss of skin firmness or to increase skin firmness. Advantageously, the lupin peptide extract can prevent the onset of dimpling and/or reduce skin dimpling.

BACKGROUND OF THE INVENTION

The dermis is one of the three constituent layers of the skin contained between the epidermis and hypodermis. The dermis is conjunctive tissue underpinning the skin and is chiefly composed of an extracellular matrix (ECM) produced by fibroblasts which are the main cell population of the dermis.

The extracellular matrix is composed of protein fibres (collagen and elastin) and of an extrafibrillar matrix also known as the fundamental substance comprising inter alia structural glycoproteins (fibronectin) and proteoglycans/glycosaminoglycans. Collagens represent about 70% of ECM components with type-I collagen in majority (85 to 90% of dermal collagen) and type-III collagen (10-15% of dermal collagen). Collagens impart firmness to the dermis with resistance to pressure (mechanical strength of the skin). Elastin fibres impart elastic properties thereto.

While collagens are essential for maintaining skin firmness, the role of the epidermal-dermal junction (EDJ) is not to be neglected. The EDJ is a complex structure separating the dermis from the epidermis. Its chief functions are those of providing mechanical support for adhesion of the epidermis to the dermis, and acting as diffusion barrier and exchange region between the two compartments. Adhesion of the epidermis to the dermis is ensured inter alia by anchoring proteins such as type-IV collagens or laminin 5. When the dermis adheres less to the epidermis, the skin loses firmness and the epidermis slackens and creases.

Glycation is a well-known phenomenon at skin level, in particular at the dermis. It is a spontaneous, non-enzymatic reaction between an amine group, in particular an amine group of an amino acid forming the proteins e.g. lysine, and a reducing sugar such as glucose or ribose.

At the dermis, glucose particularly reacts with collagen and/or elastin to yield compounds causing so-called "advanced glycation end products", well-known under the abbreviation "AGEs". These chemical modifications are not without consequences on the properties of collagen and/or elastin. For example, AGEs induce the formation of molecular bridging between the collagen fibres. These bridges deteriorate the mechanical properties of the collagen fibres by making them more rigid.

The glycation phenomenon may therefore affect the proteins of the dermal extracellular matrix such as collagen and thereby deteriorate the metabolic and mechanical properties thereof.

At skin level, since glycation deteriorates the organisation of collagen fibres and the functionalities of the dermal fibroblasts (such as the ability to contract within collagen lattices), loss of tissue firmness and elasticity is observed. The skin loses it firmness and becomes slackened. Glycation of proteins, and of collagen in particular, therefore leads to harmful consequences for the skin. These consequences can be visibly seen and may be more or less unsightly. In particular, being less structured, less firm the dermal tissue has lesser resistance against the growth of adipocytes located in the hypodermis, creating a dimpled appearance known as "orange peel".

There is therefore a need to find agents allowing the prevention of loss of skin firmness or an increase in skin firmness. Advantageously, said agent would allow the prevented onset of skin dimpling or a reduction in the orange peel appearance of the skin, in particular in persons with cellulite.

BRIEF DESCRIPTION OF THE INVENTION

The invention is directed towards the use of a lupin peptide extract to prevent loss of skin firmness or to increase skin firmness, preferably the body skin.

The invention also relates to the use of a cosmetic composition comprising 0.001 to 30% by dry weight of a lupin peptide extract to prevent loss of skin firmness or to increase skin firmness, preferably of body skin.

DETAILED DESCRIPTION OF THE INVENTION

Figure 1:
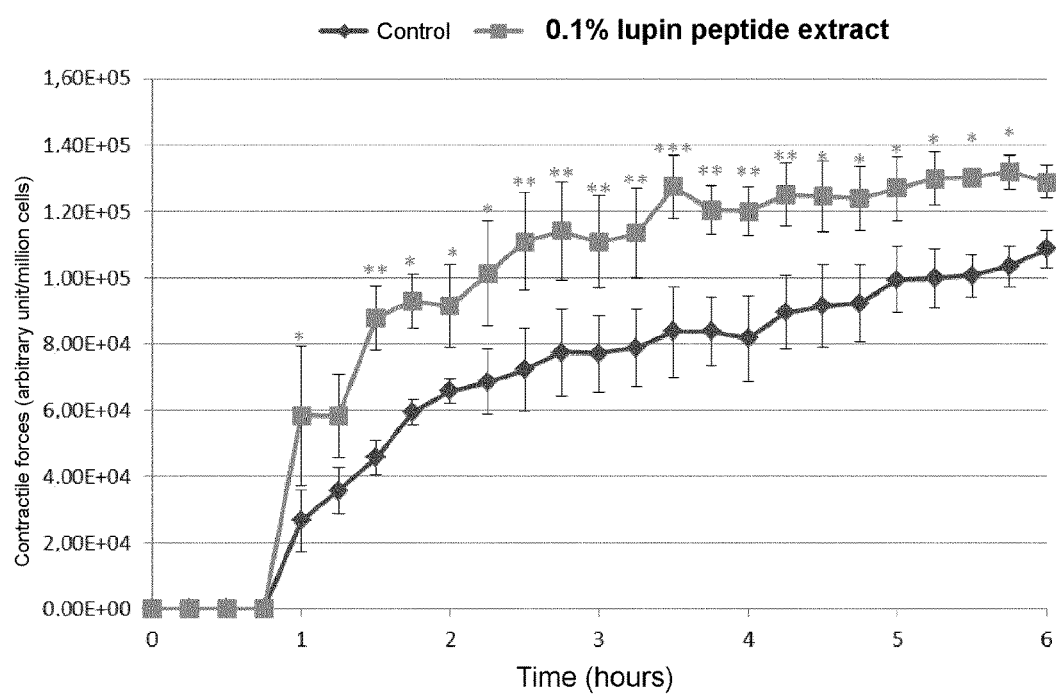
FIGS. 1 and 2: Contractile forces developed by the fibroblasts within a dermal equivalent tensioned in the GlasBox® system.

Lupin peptide extracts are known to have anti-metalloprotease activity, in particular anti-collagenase and anti-gelatinase. On the basis of this activity, it has been proposed to make use thereof to treat diseases related to excessive destruction of collagen and/or excessive destruction of supporting tissues. For example, it has been proposed to use lupin peptide extracts to treat arthritis, periodontal disease, skin lesions, inflammatory diseases, diseases related to healing deficiency, tooth enamel attack, tumour or pathological angiogenesis or the treatment of skin lesions due to intrinsic ageing of the skin, ageing due to the action of sun radiation or due to the deleterious effects of tobacco, pollution and stress.

Unexpectedly, the inventors have discovered that lupin peptide extracts have the property of reducing and even inhibiting protein glycation, in particular glycation of collagen, of stimulating the expression of collagens I, III and IV that are three major macromolecules of the dermal extracellular matrix and dermal-epidermal junction, and of stimulating the contractile forces of fibroblasts.

The present invention draws advantage from these new properties and therefore concerns the use of a lupin peptide extract to prevent loss of skin firmness or to increase skin firmness. Advantageously the lupin peptide extracts of the invention are used as anti-glycation agents.

By inhibiting the glycation of collagen and by stimulating the expression of collagens I and III, lupin peptide extracts contribute towards reinforcing the extracellular matrix. The extracellular matrix being reinforced, the skin gains firmness. Additionally, by stimulating the synthesis of collagen IV, lupin peptide extracts contribute towards reinforcing adhesion of the dermis and epidermis. Finally, by protecting the dermis against loss of contraction of the contractile fibres, lupin peptide extracts contribute towards reinforcing the firmness of the skin. Lupin peptide extracts are therefore particularly efficient in preventing loss of skin firmness or increasing skin firmness, particularly the firmness of the skin of the body as opposed to the skin of the face. Body skin is less exposed to outside attack than face skin but it has its enemies too: sedentary lifestyle, variations in weight, pregnancies, hormonal changes. . . . These phenomena can lead to loss of skin firmness or tonicity, generating the onset of unattractive disorders such as slackened skin, dimpling, cellulite.

The term cellulite refers to a localised skin disorder caused by subcutaneous fat protruding into the dermis, resulting in structural and architectural changes characterized visually by irregular dimpling.

The peptide extracts of the invention are advantageously used as specific body care products, in particular as slimming products or for their body firming and silhouette remodelling effect, toning and anti-slackening effect, anti-cellulite and/or anti-dimpling effect.

In addition, the extracellular matrix being reinforced, the dermal tissue becomes more resistant against the growth of adipocytes. The onset of dimpling is thereby hampered. Lupin peptide extracts therefore prove to be particularly effective in preventing the onset of skin dimpling and/or in reducing skin dimpling.

According to a study by Kligman et al [J Dermatolog Treat, 1999; 10 119-25] evaluating the efficacy of retinol on cellulite, this efficacy is chiefly related to restructuring of the dermis and to increased micro-vascularisation.

Therefore, action on the dermis to reinforce skin structure and promote skin firmness appears to be of primary importance to improve the appearance of cellulite.

The lupin peptide extract useful for the present invention comprises at least 80 weight % of peptides relative to the total dry weight of the peptide extract, typically 80 to 100 weight % of peptides relative to the total dry weight of the peptide extract.

The peptide extract is essentially free of sugars and lipids.

The sugar content is typically less than 4% by dry weight, preferably between 0 even 1 and 3 weight % relative to the total dry weight of the peptide extract.

The lipid content is typically less than 1% by dry weight relative to the total dry weight of the peptide extract.

The lupin peptide extract can be selected from among peptide extracts derived from lupin belonging to the genii *lupinus albus, lupinus luteus, lupinus mutabilis* and a mixture thereof. Preferably, the peptide extract is a peptide extract of sweet white lupin (*lupinus albus*), e.g. the Ares variety. Lupin of the Ares variety has a low alkaloid content.

The lupin peptide extract can be obtained using a method comprising the following steps:
 (a) extracting the lupin protein fraction;
 (b) hydrolysing the protein fraction obtained at step (a)-;
 (c) recovering a peptide extract.

Hydrolysis is typically performed via enzymatic hydrolysis. In particular, enzymatic hydrolysis can be conducted using proteases e.g. Alcalase® (NOVO NORDISK) or Prolyve 1000 (LYVEN). Enzymatic hydrolysis can be conducted at a temperature ranging from 50 to 60° C. for a time varying from 2 hours to 4 hours.

The peptides of the peptide extract advantageously have a molecular weight ranging from 130 to 10,000 Da, preferably ranging from 130 to 3500 Da, more preferably from 300 to 3500 Da.

According to one particular characteristic of the invention, 40 to 55% of the peptides of the peptide extract have a molecular weight ranging from 300 to 1200 Da, and/or 25 to 40% of the peptides of said peptide extract have a molecular weight ranging from 1200 to 3500 Da.

The peptide extract obtained at step (b) can be purified by diafiltration, preferably on an ultrafiltration module having a cut-off threshold ranging from 10,000 daltons to 15,000 daltons. Ultrafiltration allows removal of the proteins. Therefore, the method to prepare the peptide extract may comprise an ultrafiltration step. It may also comprise a nanofiltration step, e.g. on a nanofiltration module having a cut-off threshold ranging from 100 to 300 Da, or from 130 to 300 Da. Nanofiltration allows removal of the free amino acids or mineral salts.

Before packaging, the peptide extract can be sterilely microfiltered (0.2 μm) and then:
 dispensed under laminar flow into sterile containers without preserving agent; or
 microbiologically stabilised through the addition of preserving agents before being dispensed into "clean" containers. Preserving agents that can possibly be used include for example a mixture of parabens and/or Phenoxyethanol (e.g. 0.5% Phenonip). A paraben-free mixture is preferred e.g. the mixture Phenoxyethanol (1%), citric acid (0.5%), ascorbic acid (0.08%); or
 stabilised by drying via spray- or freeze-drying to obtain a peptide extract in dry form that can be packaged in hermetically sealed sachets protected against humidity and microbial contamination.

Therefore, the method to prepare the peptide extract may further comprise a concentration step of the hydrolysed peptide extract obtained at step (c) via full or partial evaporation of water.

Drying can be carried out by spray- or freeze-drying, whether or not in the presence of a substrate such as maltodextrin. Preferably, drying is obtained by freeze-drying without a substrate.

The extraction of the protein fraction can be obtained in the following manner:
 i) extracting the lipids from lupin seed using a suitable solvent and recovering the lupin protein and saccharide fractions;
 ii) extracting the protein fraction via ultrafiltration and recovering said protein fraction.

The solvent used at step i) is advantageously selected from the group of non-toxic food solvents, ethanol in particular. Extraction of the lipids is preferably obtained from lupin seeds in the form of a cake of ground lupin, or micronized lupin flour. Extraction can also be carried out using hexane.

In some embodiments, the lupin peptide extract has the amino acid composition given in following Table A (weight percentage relative to the total weight of amino acids):

TABLE A

| Amino acids | Weight % relative to the total weight of amino acids |
|---|---|
| ASP | 11.3 |
| GLU | 23.2 |
| SER | 5.1 |
| HIS | 1.7 |
| GLY | 3.4 |
| THR | 3.2 |
| ALA | 2.8 |
| ARG | 10.3 |
| TIR | 6.1 |
| CYS-CYS | 2.4 |
| VAL | 3.8 |
| MET | 0.2 |
| PHE | 16.0 |
| ILE | 3.3 |

TABLE A-continued

| Amino acids | Weight % relative to the total weight of amino acids |
|---|---|
| LEU | 7.9 |
| LYS | 3.7 |
| PRO | 4.4 |

The lupin peptide extract is intended for cosmetic (non-therapeutic) use, preferably in a topical application to the skin or taken via oral route.

The lupin peptide extract can be formulated in the form of a cosmetic composition. Therefore, the present invention also concerns the use of a cosmetic composition comprising a lupin peptide extract to prevent loss of skin firmness or to increase skin firmness, in particular the skin of the body as opposed to the face skin. Advantageously, the cosmetic composition comprising a lupin peptide extract can be used to prevent the onset of dimpling or to reduce dimpling of the skin, in particular in persons with cellulite.

The cosmetic composition may comprise 0.001 to 30%, preferably 0.01 to 5% by weight, preferably 0.05 to 5% by dry weight of lupin peptide extract relative to the total weight of the composition. Advantageously, the composition of the invention comprises 0.01 to 0.2% by weight, more advantageously 0.05 to 0.2% by weight, typically 0.01 to 0.15% by weight, particularly 0.05 to 0.15% by weight of lupin peptide extract relative to the total weight of the composition. Said concentrations can form efficient concentrations of lupin peptide extract.

In addition, the cosmetic composition may contain usual adjuvants used in the cosmetic field, such as gelling agents e.g. hydrophilic or lipophilic gelling agents, preserving agents, anti-oxidants, solvents, perfumes, fillers, chemical or mineral filters, pigments, chelating agents, odour absorbers, thermal water and/or colouring materials. The amounts of these different adjuvants are those conventionally used in cosmetics. For example, the amount of each adjuvant may vary from 0.01% to 20% by weight relative to the total weight of the cosmetic composition.

The cosmetic composition may further comprise active ingredients selected from among firming agents, draining agents, toning agents, tightening agents or mixtures thereof. The individual amount of each active ingredient may vary from 0.01% to 20% by weight relative to the total weight of the cosmetic composition.

The cosmetic composition may be in any form usually used in the cosmetic field, in particular in any form adapted for external topical application. Therefore, the cosmetic composition may be in the form of a hydroalcoholic or oil solution, an oil-in-water or water-in-oil or multiple emulsion, an aqueous or oil gel, a liquid, paste or solid anhydrous product, or a dispersion of oil in an aqueous phase by means of spherules, the spherules possibly being polymeric nanoparticles such as nanospheres and nanocapsules, or lipid vesicles of ionic and/or non-ionic type. The cosmetic composition may be more or less fluid, in the form of a cream, ointment, milk, lotion, unguent, serum, paste, foam, aerosol or stick.

When the cosmetic composition is an emulsion, the proportion of the fat phase may range from 5% to 80% by weight, preferably 5% to 50% by weight, relative to the total weight of the cosmetic competition. The oils, emulsifiers and co-emulsifiers used in the cosmetic composition are selected from among those traditionally used in the cosmetic field. The emulsifier and co-emulsifier can be contained in the composition in a proportion ranging from 0.3% to 30% by weight, preferably 0.5% to 20% by weight relative to the total weight of the cosmetic composition. The oils can be selected from among mineral oils, plant oils (apricot, sunflower seed, plum oil), animal oils, synthetic oils, silicone oils and fluorinated oils (perfluoropolyethers). Fatty alcohols such as cetyl alcohol, fatty acids or waxes such as beeswax can also be used as fats. The emulsifiers and co-emulsifiers can be selected from among esters of fatty acids and polyethylene glycol, such as PEG-40 stearate or PEG-100 stearate, the esters of a fatty acid and polyol, such as glycerol stearate and sorbitan tristearate.

In some embodiments, the cosmetic composition may be in gel form. Said gel may be particularly useful as anti-dimpling slimming gel. For example, a gel of the present invention may have the following composition:

| | Wt. % relative to the total weight of the composition |
|---|---|
| WATER | qs |
| ETHANOL | 1 to 50% |
| CAFFEINE | 1 to 10% |
| CARBOMER | 0 to 2% |
| pH ADJUSTER | 0 to 2% |
| GLYCERINE | 1 to 5% |
| LUPIN PEPTIDES | 0.05 to 5% |
| PRESERVING AGENTS | 0 to 2% |

In some embodiments, the cosmetic composition can be used as firming body care. For example, said composition may have the following composition:

| | Wt. % relative to the total weight of the composition |
|---|---|
| WATER | qs |
| ETHANOL | 1 to 50% |
| CAFFEINE | 1 to 10% |
| EMULSIFIERS | 1 to 10% |
| pH ADJUSTER | 0 to 2% |
| GLYCERINE | 1 to 5% |
| LUPIN PEPTIDES | 0.05 to 5% |
| PRESERVING AGENTS | 0 to 2% |
| OIL | 5 to 20% |
| XANTHAN GUM | 0 to 2% |
| CETYL ALCOHOL | 0 to 2% |

The lupin peptide extract and cosmetic composition comprising said extract can be used to prevent loss of skin firmness or to increase skin firmness. For example, the lupin peptide extract or cosmetic composition comprising said extract can be used in a cosmetic treatment method to prevent loss of skin firmness or to increase skin firmness, comprising the application to the skin notably the body skin of a lupin peptide extract, particularly an efficient concentration of lupin peptide extract or a composition comprising said extract.

The lupin peptide extract or cosmetic composition comprising said extract can also be used in a cosmetic body-firming treatment method comprising the application to the skin of a lupin peptide extract, in particular an efficient concentration of lupin peptide extract or composition comprising said extract. The firming obtained allows remodelling of the silhouette.

The lupin peptide extract and cosmetic composition contain said extract can be used to prevent the onset of dimpling and/or to reduce the dimpled appearance of the skin. In other words, the lupin peptide extract allows a reduction in the "orange peel" appearance that may be present in the skin of persons with cellulite. The skin is thereby smoothed. For example, the lupin peptide extract or the cosmetic composition comprising said extract can be used in a cosmetic treatment method to prevent the onset of dimpling and/or to reduce the dimpled appearance of the skin, comprising the application of the lupin peptide extract to the skin notably the body skin in an efficient concentration of lupin peptide extract or of a composition comprising said extract.

The cosmetic treatment methods such as described above are also the subject of the present invention.

EXAMPLES

The peptide extract used in the examples below is such as supplied by Laboratoires Expanscience under the trade name ACTIMP® (powder) or ACTIMP® 1.9.3 (liquid).

It can be prepared in the following manner.

1. Preparation of Lupin Peptide Extracts

Preparation of Ground, Delipidated Lupin Cake

The lupin seeds are ground and the lipids extracted using ethanol.

Extraction and Purification of Lupin Proteins

This step comprises aqueous solubilisation of the soluble fraction at alkaline pH followed by separation of the insolubles.

From the ground delipidated lupin cake, the proteins are extracted at pH 9.0 (pH adjusted by addition of sodium hydroxide) with a flour/water ratio of 1/10 (w/w). The solution is incubated under agitation at ambient temperature for one hour. The insoluble part of the cake is separated from the soluble part by dewatering. The cake obtained is washed. The soluble fraction containing the proteins and soluble sugars is diafiltered on an ultrafiltration module with a cut-off threshold of 10.000 Daltons to separate the proteins (retentate) from the soluble sugars (ultrafiltrate).

Production and Purification of Peptides by Enzymatic Hydrolysis:

The ultrafiltration retentate containing the proteins is adjusted to a concentration of 100 g/l and then hydrolysed to pH 8.0 in the presence of Alcalase# (NOVO NORDISK) at 55° C. for about 3 h. After hydrolysis, the enzyme is denatured by hydrolysis for 15 min at 85° C. As soon as the solution has cooled, it is neutralised through the addition of hydrochloric acid. The peptides obtained are purified by diafiltration on an ultrafiltration module having a cut-off threshold of 10,000 Daltons. The solution obtained is nano-filtered for desalting (removal of sodium chloride) and to concentrate the peptide fraction. The solution of peptides is decoloured using 3% activated carbon (1 hour at 50° C.), the carbon being removed by filtration.

Sterilisation and Stabilisation of the Peptide Fraction:

Before packaging, the solution is sterilely microfiltered (0.2 μm) and can then be:

stabilised microbiologically through the addition of a paraben-free mixture (Phenoxyethanol (1%), citric acid (0.5%), sorbic acid (0.08%)) before being dispensed into "clean" containers (Actimp®1.9.3 (formed of 10% lupin peptides) marketed by Laboratoires Expanscience)

stabilised by freeze-drying to obtain peptides in dry form, packaged in sealed sachets protected against humidity and microbial contamination (Actimp® powder, marketed by Laboratoires Expanscience).

The dry extract and hence the active portion has the following characteristics:

Appearance: homogenous, non-hygroscopic powder;
Colour: off-white;
Chemical composition:
Total sugar content (assay with anthrone): <4%
Chloride content (Kit SIGMA ref: 955-30): <6° A
Water content (100° C., 4 h): <8%
Peptide content: ≥80%
pH (solution at 20 g/l): 7.06
Solubility (osmotic water): >100 g/L

TABLE 1

| Amino acid composition of the hydrolysate | | | | | |
|---|---|---|---|---|---|
| Amino acids | A.A. Mol wt. | Conc. in mM | Conc. in mg/l | % in powder | %/Total AAs |
| ASP | 133.1 | 2.078 | 276.582 | 9.9 | 11.3 |
| GLU | 147.1 | 3.858 | 567.438 | 20.3 | 23.2 |
| SER | 105.1 | 1.196 | 125.647 | 4.5 | 5.1 |
| HIS | 155.2 | 0.270 | 41.904 | 1.5 | 1.7 |
| GLY | 75.1 | 1.114 | 83.624 | 3.0 | 3.4 |
| THR | 119.1 | 0.664 | 79.023 | 2.8 | 3.2 |
| ALA | 89.1 | 0.763 | 67.983 | 2.4 | 2.8 |
| ARG | 174.2 | 1.447 | 251.980 | 9.0 | 10.3 |
| TYR | 181.2 | 0.829 | 150.215 | 5.4 | 6.1 |
| CYS-CYS | 240.3 | 0.247 | 59.234 | 2.1 | 2.4 |
| VAL | 117.1 | 0.792 | 92.743 | 3.3 | 3.8 |
| MET | 149.2 | 0.029 | 4.327 | 0.2 | 0.2 |
| PHE | 165.2 | 1.044 | 172.469 | 6.2 | 7.0 |
| ILE | 131.2 | 0.621 | 81.410 | 2.9 | 3.3 |
| LEU | 131.2 | 1.481 | 194.307 | 6.9 | 7.9 |
| LYS | 146.2 | 0.626 | 91.448 | 3.3 | 3.7 |
| PRO | 115.1 | 0.935 | 107.619 | 3.8 | 4.4 |
| | | | 2447.952 | | |
| Total | | | | 87.4% | |

In the above-described tests, the peptide extract was solubilised in the culture medium so that it could be applied to the cells and explants at concentrations of 0.1%, 0.2% and/or 2%.

2. Evidencing of the Effects of Lupin Peptide Extract on Glycation

The non-enzymatic insertion of AGEs in synthesised collagen fibres deposited by human dermal fibroblasts cultured in vitro was examined. A radioactive detection method was used that was based on the incorporation of tritiated glucose in the proteins of the extracellular matrix.

Normal human dermal fibroblasts were cultured in the presence of vitamin C to stimulate the synthesis of collagen. The cells then underwent different operations (freezing/thawing/heating) to inactivate all enzymatic activity.

The matrix layers thus obtained were treated in the presence of the above-described lupin peptide extract at 0.2 and 2%, aminoguanidine HCl at 1 mg/ml (control), 0.2% glucose and [$^3$H]-glucose radioactive marker for 15 days at 37° C., in the absence of oxygen (rapid re-oxygenation was performed after 7 treatment days).

After incubation, the proteins of the extracellular matrix (chiefly collagens) were extracted using a chaotropic buffer, precipitated with trichloroacetic acid and collected on filters. The radioactivity incorporated in the ECM fibres was measured by liquid scintillation.

The results were analysed statistically using one-factor analysis of variance followed by a Dunnett test, and are given in the Table below:

|  | Incorporation [$^3$H]-glucose (cpm) | Inhibition of glycation |
| --- | --- | --- |
| Control | 5527 ± 464 |  |
| Aminoguanidine 1 mg/ml | 1219 ± 92 | −78% $p < 0.001$ |
| 0.2% lupin peptide extract | 4466 ± 655 | −19% ns |
| 2% lupin peptide extract | 3338 ± 465 | −40% $p < 0.05$ |

Effect of [$^3$H]-glucose on non-enzymatic glycation

The results show a protective effect of lupin peptide extract against glycation. The lupin peptide extract protects the extracellular matrix of the dermis against glycation. Lupin peptide extract is therefore capable of preventing rigidifying of the matrix to preserve the elasticity and firmness of the skin (protection of the biomechanical properties of collagen).

3. Evidencing of the Effects of Lupin Peptide Extract on Contractile Forces

A model of dermal equivalents containing fibroblasts allows evaluation of the quality of interactions between fibroblasts and collagen fibres. The free contraction/retraction of these dermal equivalents results from the dynamic activity of the cells which apply tensile forces on the collagen network.

The effect of lupin peptide extract on the contraction of dermal equivalents was evaluated. To induce a condition of fibroblast loss of contractile forces, the dermal equivalents were seeded with senescent so-called "aged" fibroblasts (obtained by successive passaging in accordance with the Hayflick model).

"Aged" or normal dermal equivalents were prepared by mixing the fibroblasts (at passage 8 for normal dermal equivalents or at passage 17 for "aged" dermal equivalents) with a collagen solution.

After full gelling, the dermal equivalents were treated with TGFβ at 10 ng/ml (control) or 0.1% lupin peptide extract and incubated for 4 days.

The dermal equivalents were photographed at D1, D3 and D4 to measure their surface area for determination of contraction.

The results were statistically analysed using Student's t test and are given in the Table below.

TGFβ stimulates the contraction of "aged" DEs, this stimulation becoming significant after a treatment time of 4 days; this result validates the assay.

0.1% lupin peptide extract significantly stimulates the contraction of "aged" DEs as soon as the 1st day of treatment.

It allows early counteracting of the effect of ageing on the "slackening" of dermal equivalents.

Lupin peptide extract inhibits "slackening" of the dermal equivalents induced here by ageing of the cells.

By protecting the dermis against loss of contraction, lupin peptide extract contributes towards maintaining the elastic properties of the skin to obtain a "tightening" effect and the maintaining of skin firmness.

4. Evidencing of the Effects of Lupin Peptide Extract on Isometric Forces

The effect of lupin peptide extract was researched on the isometric forces developed by dermal fibroblasts in a tensioned dermal equivalent (GlasBox® model).

The GlasBox® system (Growing LAttice Study BOX) allows the measurement, in a tensioned dermal equivalent, of the contractile forces developed by the fibroblasts. These indicate the activity of the fibroblasts in reorganising the matrix.

In the GlasBox® system, the dermal equivalents develop under tensile forces between two slides which also act as sensors: under the influence of the retraction force developed by the fibroblasts, the slides become deformed. This translates as a variation in the electrical resistance of the strain gauge. This variation, indicating the force developed within the dermal equivalent, is measured in real time.

Dermal equivalents were prepared by mixing normal human dermal fibroblasts with a collagen solution. This mixture was poured into the rectangular wells of the GlasBox®. After formation of a gel, the medium containing or not containing the 0.1% lupin peptide extract was added, The isometric forces were measured over 24 hours.

Figure 2:
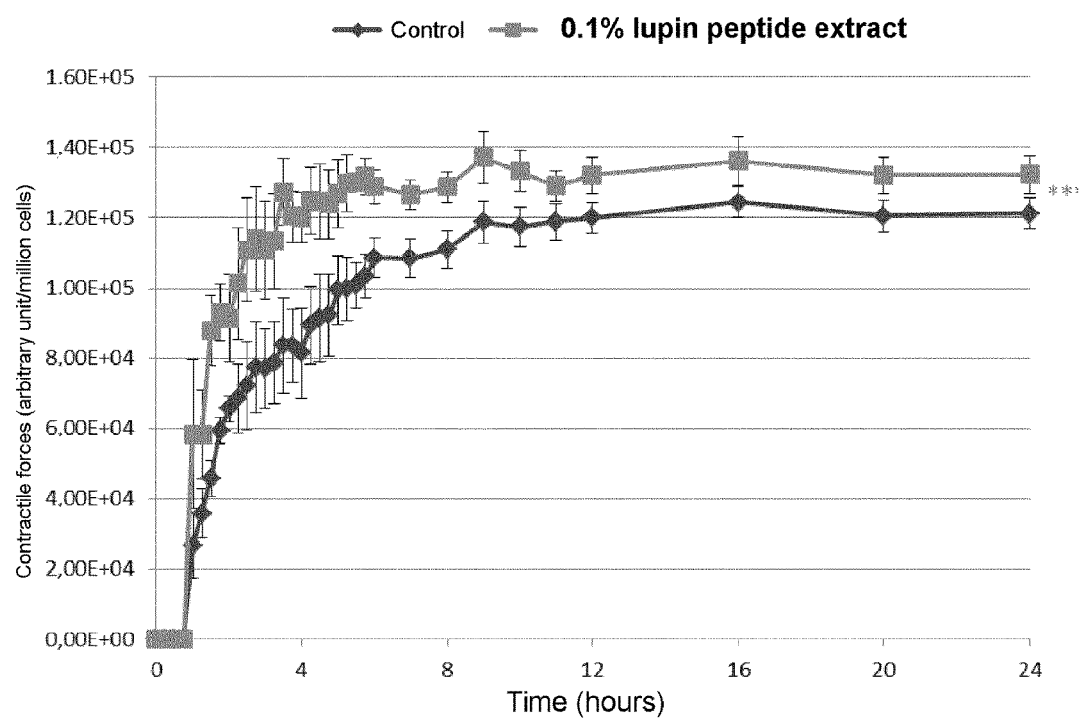

The results were analysed statistically using two-factor analysis of variance followed by a Fisher test, and are given in FIGS. 1 and 2.

|  |  | Control (Normal DEs) | Control ("Aged" DEs) | TGFβ 10 ng/ml | 0.1% lupin peptide extract |
| --- | --- | --- | --- | --- | --- |
| D1 | Area in mm$^2$ (mean ± SEM) | 284.9 ± 2.9 | 282.7 ± 6.2 | 264.6 ± 5.5 | 243.1 ± 3.9 |
|  | % "aged" control | 101 | 100 | 94 | 86 ($p < 0.01$) |
| D3 | Area in mm$^2$ (mean ± SEM) | 283.6 ± 11.6 | 300.1 ± 13.1 | 285.9 ± 6.7 | 248.5 ± 1.5 |
|  | % "aged" control | 95 | 100 | 95 | 83 ($p < 0.05$) |
| D4 | Area in mm$^2$ (mean ± SEM) | 205.0 ± 5.3 | 237.7 ± 2.6 | 201.3 ± 8.4 | 217.5 ± 2.7 |
|  | % "aged" control | 86 ($p < 0.01$) | 100 | 85 ($p < 0.05$) | 92 ($p < 0.01$) |

Changes in the contraction of normal or "aged" dermal equivalents

Overall, the contraction of the "aged" dermal equivalents (DEs) is lower than that of the normal DEs (the surface area of "aged" DEs is larger), reflecting the decrease in fibroblast/collagen fibre interaction induced by ageing of the cells.

Overall, the 0.1% lupin peptide extract significantly increased the forces developed by the fibroblasts. This increase is more particularly significant in the first part of the curve (after 1 hour and up to 5.75 measuring hours).

This shows a tightening effect of lupin peptide extract, in particular during the early phase of matrix reorganisation by the fibroblasts.

The forces developed by the fibroblasts within a tensioned dermal equivalent are significantly stimulated by lupin peptide extract. These results evidence a tightening effect of lupin peptide extract to combat loss of skin firmness and elasticity.

5. Evidencing of the Effects of Lupin Peptide Extract on the Expression of Collagens I, III and IV and Laminin 5

The activity of lupin peptide extract was evaluated on explants of human skin: markers of the dermal extracellular matrix (Collagens I and III) and of the epidermal-dermal junction (Collagen IV, laminin 5) were analysed by immunostaining.

0.2% lupin peptide extract was applied to the surface of explants of normal human skin explants maintained in survival.

After 7 to 10 days' treatment, the skin explants were collected and frozen to −80° C. or fixed and included in paraffin.

Immunostaining of different markers of the dermal matrix or epidermal-dermal junction was performed on skin sections:

Collagens I and IV, and laminin 5 were stained on frozen sections and detected under fluorescence (FITC), the nuclei were counter-stained with propidium iodide.

Collagen III was stained on paraffin section and detected using peroxidase.

Staining was visualised under microscopy and quantified by image analysis.

The variations in staining intensity were analysed statistically using Student's t test.

Figure 3:
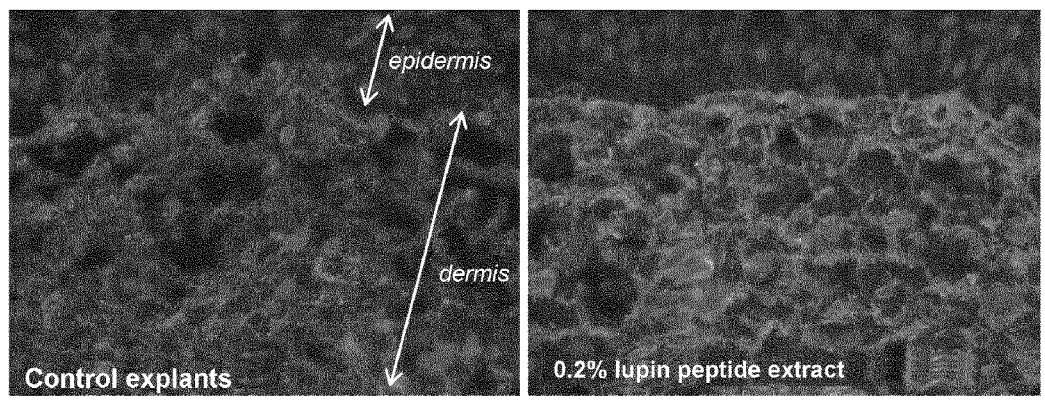
FIG. 3: Expression of type-I Collagen (Dermis).
Figure 4:
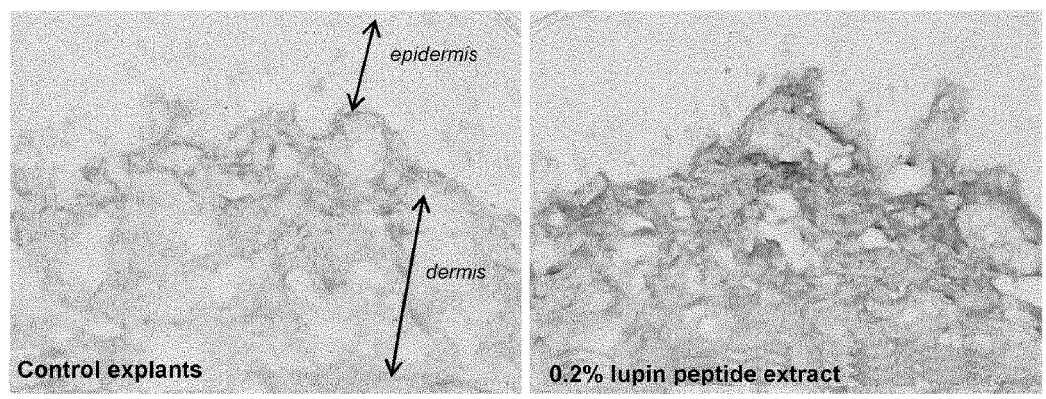
FIG. 4: Expression of type-III Collagen (Dermis).
Figure 5:
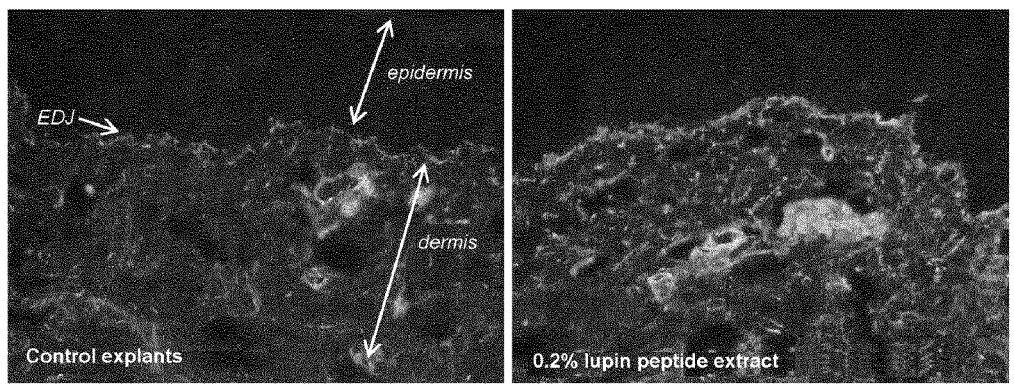
FIG. 5: Expression of type-IV Collagen (EDJ).

The results are given in FIGS. 3 to 5.

Lupin peptide extract induced intensification of the staining of collagen I after 7 and 10 treatment days (FIG. 3).

| | Collagen I (surface %) | | | |
|---|---|---|---|---|
| | D7 | | D10 | |
| Control explants | 28.0 ± 7.2 | | 21.9 ± 6.4 | |
| 0.2% lupin peptide extract | 37.7 ± 7.6 | +34% $p < 0.05$ | 44.2 ± 6.8 | +102% $p < 0.001$ |

Quantification by image analysis of Collagen I staining in the papillary dermis

Lupin peptide extract induces intensification of the staining of collagen III after 7 and 10 treatment days (FIG. 4).

| | Collagen III (surface %) | | | |
|---|---|---|---|---|
| | D7 | | D10 | |
| Control explants | 30.9 ± 12.2 | | 28.3 ± 8.1 | |
| 0.2% lupin peptide extract | 51.3 ± 12.4 | +66% $p < 0.01$ | 49.8 ± 9.6 | +76% $p < 0.001$ |

Quantification by image analysis of Collagen III staining in the papillary dermis Lupin peptide extract induces intensification of the staining of collagen IV at the EDJ after 7 and 10 treatment days (FIG. 5).

| | Collagen IV (surface %) | | | |
|---|---|---|---|---|
| | D7 | | D10 | |
| Control explants | 22.0 ± 3.5 | | 14.1 ± 4.0 | |
| 0.2% lupin peptide extract | 29.8 ± 8.3 | +35% $p < 0.05$ | 44.9 ± 14.5 | +219% $p < 0.001$ |

Quantification by image analysis of Collagen IV staining in the EDJ.

Figure 6:
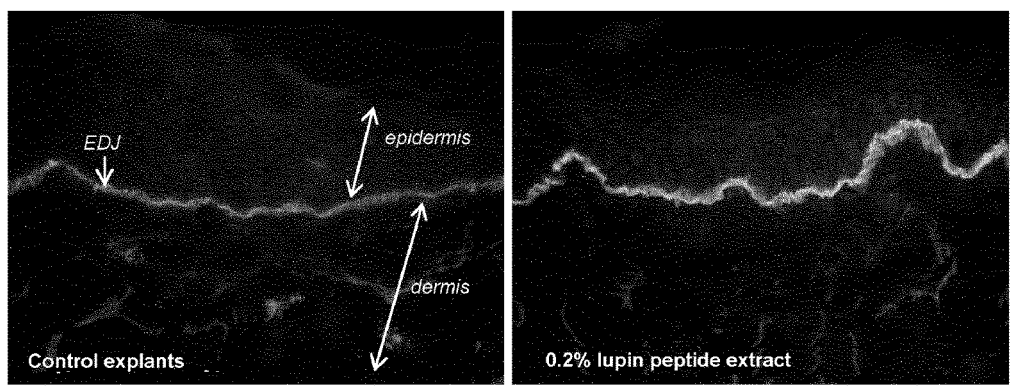
FIG. 6: Expression of laminin 5 (EDJ).

Lupin peptide extract induces intensification of the staining of laminin 5 at the EDJ after 7 and 10 treatment days (FIG. 6).

| | Laminin 5 (surface %) at D7 | |
|---|---|---|
| Control explants | 18.4 ± 5.1 | |
| 0.2% lupin peptides | 24.2 ± 4.4 | +31% $p < 0.05$ |

Quantification by image analysis of laminin 5 staining in the EDJ

The topical application of lupin peptide extract to skin explants stimulated the expression of collagens I and III, two major macromolecules of the dermal extracellular matrix, and stimulated the expression of collagen IV and laminin 5, markers of the epidermal-dermal junction.

Lupin peptide extract is therefore capable of reinforcing the epidermal-dermal junction and the dermal extracellular matrix to promote properties of skin firmness and tonicity.

The invention claimed is:

1. A method for preventing loss of skin firmness caused by glycation or increasing glycation affected skin firmness, comprising administering an effective amount of lupin peptide extract as an anti-glycation agent to a subject in need thereof, wherein said lupin peptide extract is obtained by enzymatic hydrolysis and comprises at least 80 weight % of peptides relative to the total dry weight of the peptide extract.

2. The method of claim 1 for further preventing the onset of skin dimpling caused by glycation or reducing skin dimpling caused by glycation.

3. A method for remodeling the glycation affected body silhouette, comprising administering an effective amount of lupin peptide extract as an anti-glycation agent to a subject in need thereof, wherein said lupin peptide extract is obtained by enzymatic hydrolysis and comprises at least 80 weight % of peptides relative to the total dry weight of the peptide extract.

4. The method of claim 1, wherein the peptides of said lupin peptide extract have a molecule weight of less than 10,000 Da.

5. The method of claim 1, wherein the peptide extract comprises less than 4% by weight of sugars and/or comprises less than 1% by weight of lipids.

6. The method of claim 1, wherein the peptides of the peptide extract have a molecular weight higher than 130 Da.

7. The method of claim 1, wherein the peptide extract is a peptide extract of *lupinus albus*.

8. The method of claim 1, wherein the lupin peptide extract is able to be obtained using a method comprising the following steps:
 (a) extracting the lupin protein fraction;
 (b) hydrolysing the protein fraction obtained at step a) by enzymatic hydrolysis;
 (c) recovering the hydrolysed peptide extract.

9. The method of claim 1 or 3 in topical application or taken via oral route.

10. A method for preventing loss of skin firmness caused by glycation or for increasing glycation affected skin firmness, comprising administering an effective amount of a cosmetic composition comprising 0.001 to 30% by dry weight of lupin peptide extract as an anti-glycation agent, wherein said lupin peptide extract is obtained by enzymatic hydrolysis and comprises at least 80 weight % of peptides relative to the total dry weight of the peptide extract.

11. The method of claim 10, wherein the cosmetic composition further comprises gelling agents, preserving agents, anti-oxidants, solvents, perfumes, fillers, chemical or mineral filters, pigments, chelating agents, odour absorbers, thermal water and/or colouring materials.

12. The method according to claim 3, wherein said lupin peptide extract comprises at least 80 weight % of peptides relative to the total dry weight of the peptide extract.

13. The method according to claim 3, wherein the peptides of said lupin peptide extract have a molecule weight of less than 10,000 Da.

14. The method according to claim 3, wherein the peptide extract comprises less than 4% by weight of sugars and/or comprises less than 1% by weight of lipids.

15. The method according to claim 3, wherein the peptides of the peptide extract have a molecular weight higher than 130 Da.

16. The method according to claim 3, wherein the peptide extract is a peptide extract of *lupinus albus*.

17. The method according to claim 3, wherein the lupin peptide extract is able to be obtained using a method comprising the following steps:
  (a) extracting the lupin protein fraction;
  (b) hydrolysing the protein fraction obtained at step a) by enzymatic hydrolysis;
  (c) recovering the hydrolysed peptide extract.

18. The method according to claim 3 in topical application or taken via oral route.

19. The method of claim 1, wherein the skin is the body skin.

20. The method of claim 10, wherein the cosmetic composition comprises 0.05 to 0.2% by weight of lupin peptide extract.

21. The method of claim 10, wherein the skin is the body skin.

* * * * *